United States Patent
Sarwar et al.

(10) Patent No.: US 9,341,638 B2
(45) Date of Patent: May 17, 2016

(54) AUTOMATIC ANALYZER

(75) Inventors: Sayaka Sarwar, Tokyo (JP); Tatsuya Tokunaga, Tokyo (JP); Miki Taki, Tokyo (JP); Toshihide Orihashi, Tokyo (JP); Hiroki Mori, Tokyo (JP); Yoichi Aruga, Tokyo (JP); Takashi Nakasawa, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 17 days.

(21) Appl. No.: 14/122,681

(22) PCT Filed: May 22, 2012

(86) PCT No.: PCT/JP2012/063076
§ 371 (c)(1),
(2), (4) Date: Dec. 26, 2013

(87) PCT Pub. No.: WO2012/165229
PCT Pub. Date: Dec. 6, 2012

(65) Prior Publication Data
US 2014/0147335 A1 May 29, 2014

(30) Foreign Application Priority Data
Jun. 3, 2011 (JP) .................................. 2011-125759

(51) Int. Cl.
*G01N 35/00* (2006.01)
*G06Q 10/06* (2012.01)
*G06F 19/00* (2011.01)

(52) U.S. Cl.
CPC .... *G01N 35/00584* (2013.01); *G01N 35/00722* (2013.01); *G06F 19/366* (2013.01); *G06Q 10/06* (2013.01); *G01N 2035/00891* (2013.01)

(58) Field of Classification Search
CPC ........... G01N 2035/00891; G01N 2035/00914
See application file for complete search history.

(56) References Cited

U.S. PATENT DOCUMENTS

| 5,839,091 A | 11/1998 | Rhett et al. |
| 2005/0013736 A1 | 1/2005 | McKeever |

(Continued)

FOREIGN PATENT DOCUMENTS

| EP | 0973115 A2 | 1/2000 |
| EP | 1439472 A1 | 7/2004 |

(Continued)

OTHER PUBLICATIONS

International Preliminary Report on Patentability received in International Application No. PCT/JP2012/063076 dated Dec. 19, 2013.

(Continued)

*Primary Examiner* — Jill Warden
*Assistant Examiner* — Julie Tavares
(74) *Attorney, Agent, or Firm* — Mattingly & Malur, PC

(57) ABSTRACT

An automatic analyzer enables users to perform working steps easily and reliably by switching a display screen irrespective of a skill level of the user. The automatic analyzer, which determines a consistency of a test item, includes a display/input section to display a plurality of working steps relating to necessary work flow for measurement. The display/input section is adapted to selectively present a maximized workflow display and a reduced workflow display. The maximized workflow display shows a series of operations and works, and further shows a plurality of operations and works in an order that the plurality of operations and works are processed. In a reduced display of the work flow, the reduced workflow display shows details of a specific operation or work, and a position of the specific operation or work in a sequence that the entire series of operations and works are processed.

8 Claims, 6 Drawing Sheets

(56) References Cited

U.S. PATENT DOCUMENTS

| | | |
|---|---|---|
| 2005/0175506 A1 | 8/2005 | Matsubara et al. |
| 2007/0038411 A1* | 2/2007 | Taki et al. ............ 702/182 |
| 2008/0046208 A1* | 2/2008 | Okuno et al. ............ 702/81 |

FOREIGN PATENT DOCUMENTS

| | | |
|---|---|---|
| EP | 1755035 A2 | 2/2007 |
| EP | 1986013 A2 | 10/2008 |
| EP | 2040081 A2 | 3/2009 |
| JP | 10-339732 A | 12/1998 |
| JP | 2000-046835 A | 2/2000 |
| JP | 2005-195401 A | 7/2005 |
| JP | 2007-040922 A | 2/2007 |
| JP | 3990944 B2 | 7/2007 |
| JP | 2009-019913 A | 1/2009 |
| JP | 2010-197148 A | 9/2010 |
| WO | 2011037069 A1 | 3/2011 |

OTHER PUBLICATIONS

Japanese Office Action received in corresponding Japanese Application No. 2013-517985 dated Nov. 4, 2014.
Extended European Search Report received in corresponding European Application No. 127929362 dated Apr. 7, 2015.

* cited by examiner

AUTOMATIC ANALYZER

TECHNICAL FIELD

The present invention relates generally to an automatic analyzer analyzing such biological samples as of blood and urine, and more particularly to an automatic analyzer suitable for displaying job flow (work flow) at a display section.

BACKGROUND ART

While manufacturers of the automatic analyzer for analyzing such biological samples as of blood and urine have been making attempts to simplify various operations assigned to these analyzers, the user still engages in calibration, maintenance, reagent replacement, and many other operations in a manual manner before and after patient sample measurement. These successive operations and a job work flow need to be performed reliably or in the correct order. Otherwise, accurate measurement results are not likely to be output. It is vital that these operations, jobs, and working steps be properly executed in handling the medical apparatuses that need to maintain the reliability of measurement results.

For these reasons, there is a proposed method that enables even an inexperienced user to properly operate an apparatus by displaying job flow (work flow) of before and after a measurement on a screen of the apparatus, guiding the user by different color-coded representation according to mandatory work items for example, in order to reduce erroneous operations and work omissions (for example, refer to Patent Document 1).

In addition, it is known that an apparatus sets work flow, screens, and related explanations or the like to be displayed according to a particular skill level of a user (for example, refer to Patent Document 2).

PRIOR ART LITERATURE

Patent Documents

Patent Document 1: JP-3990944-B
Patent Document 1: JP-2010-197148-A

SUMMARY OF THE INVENTION

Problems to be Solved by the Invention

Since the work flow referred to here includes operations intended for various purposes, screens related to these operations are also diverse in most cases. As more functions are assigned to automatic analyzers, screen structures have becoming more complex, and the number of screens to be operated has been increasing.

On the contrary, in the methods described in Patent Documents 1 and 2, the current screens provided for displaying work flow are configured in such a manner that selecting a working step corresponding to a necessary operation will close the display screen relating to the work flow. Selecting the screen of the work flow again and then selecting a button to continue the next job will cause the screen to be switched to another screen.

Another concern is since subdividing the screen displayed after the user's skill level has been determined makes it necessary to switch login ID and change settings, even a skilled user may have a trouble in immediately switching the screen in an attempt to confirm something.

Additionally, to display a work flow on the active screen in an attempt to understand association with the work flow requires the user to display individual working steps in a smaller size, which reduces visibility and hence working efficiency.

An object of the present invention is to provide an automatic analyzer that enables every user to perform working steps easily and reliably by switching a display screen irrespective of a skill level of the user as an operator of the apparatus.

Means for Solving the Problems (1) In order to attain the above object, an automatic analyzer according to an aspect of the present invention includes means to display a plurality of working steps relating to necessary work flow for measurement and is configured to analyze a sample automatically to determine a consistency of a test item; wherein the display means is adapted to selectively present a maximized workflow display and a reduced workflow display; and wherein in a maximized display of the work flow representing a series of operations, the maximized workflow display shows a plurality of operations in an order that the plurality of operations are processed, and in a reduced display of the work flow, the reduced workflow display shows details of a specific operation or work, and a position of the specific operation or work in a sequence that the entire series of operations are processed.

Because of the above configuration, the automatic analyzer enables every user to perform working steps easily and reliably by switching the display, irrespective of the skill level of the user as an operator of the apparatus.

(2) In above paragraph (1), the reduced workflow display preferably includes a display of a working step button and scroll button to shift screen control from the displayed details of the specific operation or work to a working step immediately preceding or immediately following the operation or work.

(3) In above paragraph (1), the display means preferably displays created/stored messages along with the maximized workflow display.

(4) In above paragraph (3), each of the stored messages is preferably displayed in a selective manner according to conditions.

(5) In above paragraph (3), when the displayed messages include an unread message, this unread message is preferably displayed on the display screen in distinction from other messages.

(6) In above paragraph (1), the details and processing sequence of the working steps displayed on the maximized workflow display can be preferably edited.

(7) In above paragraph (1), information on other screens can be preferably confirmed at the same time on the reduced workflow display.

Effect of the Invention

In accordance with the present invention, the automatic analyzer enables every user to perform working flow easily and reliably by switching the display, irrespective of the skill level of the user as an operator of the apparatus.

MODE FOR CARRYING OUT THE INVENTION

Hereunder, a configuration and operation of an automatic analyzer according to an embodiment of the present invention will be described with reference to FIGS. 1 to 6.

First, the configuration of the automatic analyzer according to the embodiment of the present invention is described below referring to FIG. 1.

Figure 1:
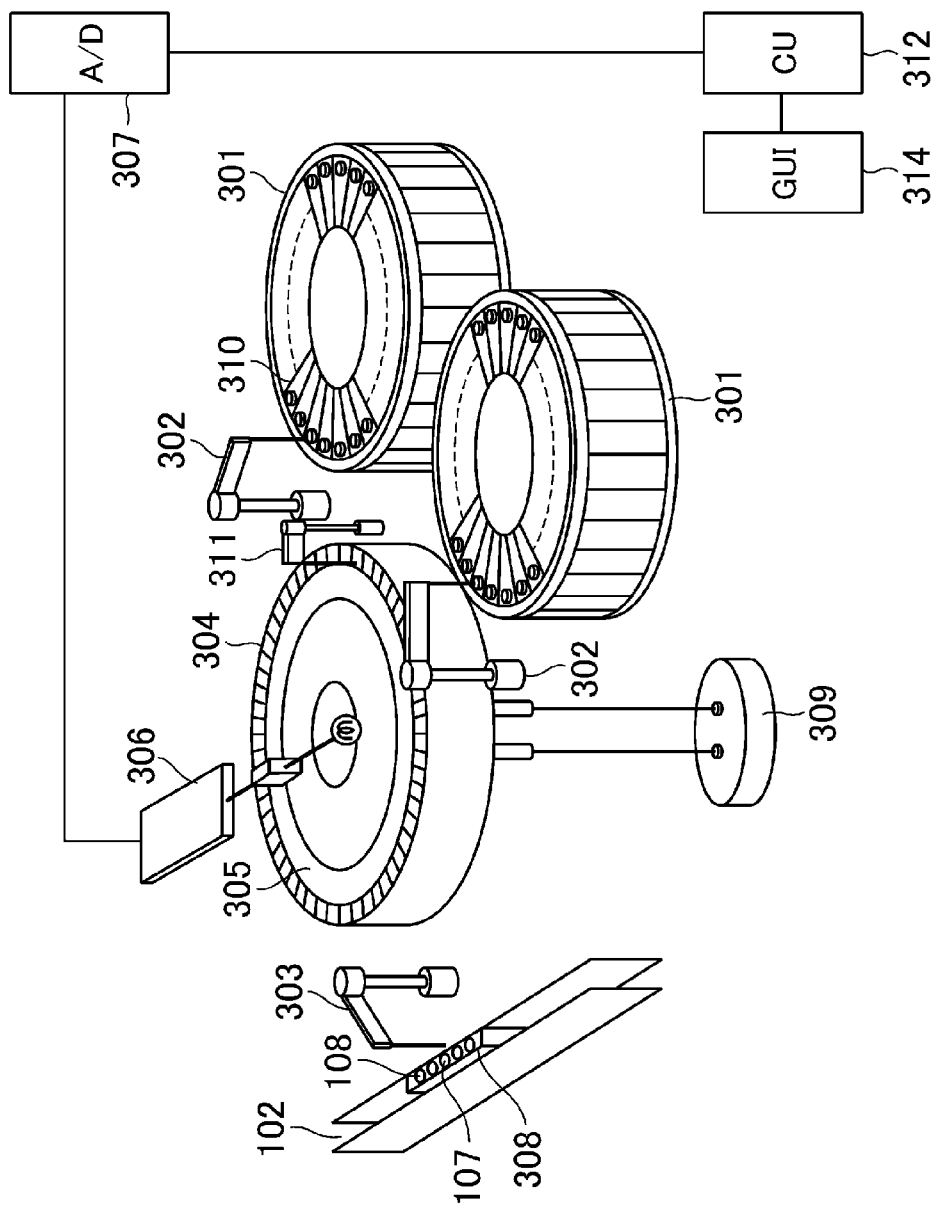
FIG. 1 is a configuration diagram of an automatic analyzer according to an embodiment of the present invention.

FIG. 1 is a configuration diagram of the automatic analyzer according to the embodiment of the present invention.

The automatic analyzer of the present embodiment mainly includes: a reagent system equipped with two reagent disks 301 which are reagent container storage units and with reagent-dispensing pipettors 302 which are provided near the two reagent disks 301; a sampling system including a sample-dispensing pipettor 303; a reaction system including a reaction disk 305 with reaction vessels 304; a measurement system including a multiwavelength photometer 306 and an analog/digital converter 307; and an operation and control system including a control unit (computer) 312 and a display/input section 314.

A rack 107 with sample containers 108 set up inside it is transported to a sample suction position 308 by a transport unit 102. The sample-dispensing pipettor 303 draws up a sample from a sample container 108 by suction and dispenses a predetermined amount of the sample into a reaction vessel 304 held by the reaction disk 305.

After the sample solution has been delivered and dispensed into the reaction vessel 304, this reaction vessel is moved to a first reagent-adding position in the reaction disk 305 connected with a constant-temperature oven 309. At this time, the reagent disk 301 rotates to move a reagent container 310 corresponding to a current analytical item to a position under a reagent-dispensing pipettor 302 held by a lifting arm. A predetermined first reagent that the reagent-dispensing pipettor 302 has drawn up by suction is then added to the sample solution in the reaction vessel 304 which has been moved to the first reagent-adding position. The reaction vessel 304 with the first reagent added to its internal contents is next moved to a position of a stirrer 311 by which a first stirring operation is carried out upon the internal contents of the reaction vessel 304.

A flux of light that has been emitted from a light source passes through the reaction vessel 304 whose internal contents have been stirred and then enters the multi-wavelength photometer 306. Absorbance of a reaction solution which is an internal content of the reaction vessel 304 is detected by the multi-wavelength photometer 306. An absorbance signal that has been derived from the detection is supplied to the control unit (computer) 312 via the analog/digital converter 307 and an interface, and then converted into a consistency for an analysis item of an analyte in the sample solution. The display/input section 314 is a graphic user interface (GUI) that is connected to the control unit 312 and displays analytical results and operation screens. Once an operation screen has been displayed on the display/input section 314, GUI can be operated by clicking buttons displayed on the operation screen by use of, for example, a mouse.

After measurement, the reaction vessel 304 is moved to a position of a reaction vessel-cleaning mechanism where the solution inside the reaction vessel is then discharged, and the reaction vessel is next cleaned with water at a cleaning position to prepare for a next analysis.

Next, an operation screen displayed on the display/input section in the automatic analyzer according to the embodiment of the present invention is described in detail below with reference to FIGS. 2 to 5.

Figure 2:
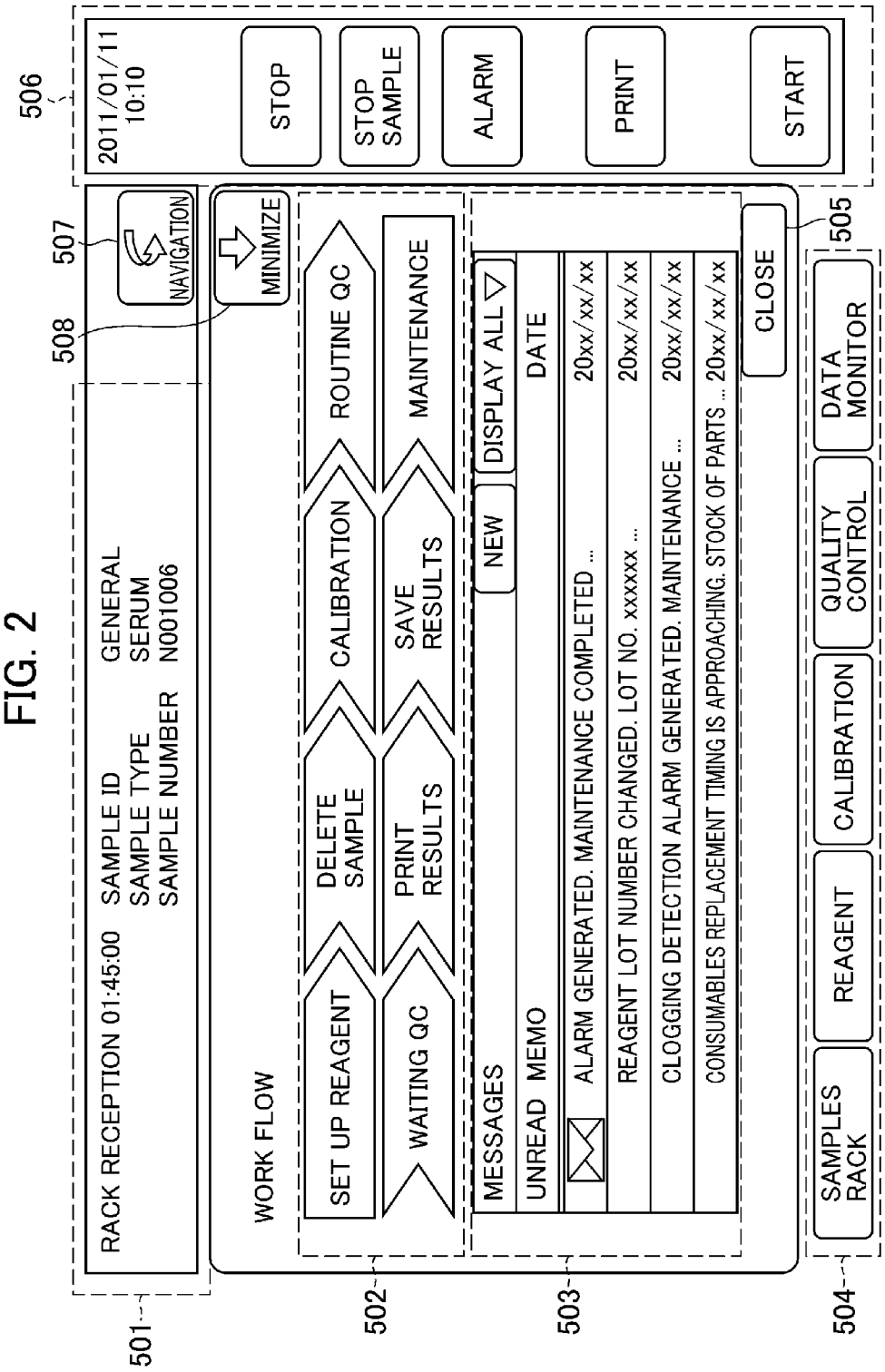
FIG. 2 is an explanatory diagram of an operation screen displayed on a display/input section in the automatic analyzer according to the embodiment of the present invention.

FIG. 2 is an explanatory diagram of an operation screen displayed on the display/input section in the automatic analyzer according to the embodiment of the present invention.

The work flow displayed on an operation screen of the automatic analyzer in the present embodiment has two forms of display mode. The first form is maximized workflow display shown in FIG. 2, and the second form is reduced workflow display shown in FIG. 4. In the maximized workflow display, when the work flow representing a series of operations and works is displayed, a plurality of operations and works are displayed in the order of their process. In the reduced workflow display, since an area needed for the display is smaller compared with a display area of the maximized workflow display, other display areas can each be correspondingly enlarged. In the reduced workflow display, therefore, when the work flow representing the series of operations and works is displayed, details of a specific operation or work in the series of operations and works to be processed are displayed with information denoting a position of the specific operation or work in a sequence that the entire series of operations and works are processed. Further details of the two display forms will be described later herein with reference to FIGS. 2 and 4. The number of operations and works which can be displayed here in further detail may be one or more. This is because the number of operations and works which can be displayed depends upon the screen composition and other factors. In the reduced workflow display, therefore, a plurality of specific operations and works in the series of operations and works to be processed may each be displayed in further detail and with information denoting a position of the specific operation or work in the sequence that the entire series of operations and works are processed. Given the same display area, when one specific operation or work is displayed alone, the specific operation or work can be displayed in a larger size than when the plurality of specific operations are displayed, and visibility is consequently enhanced.

Figure 3:
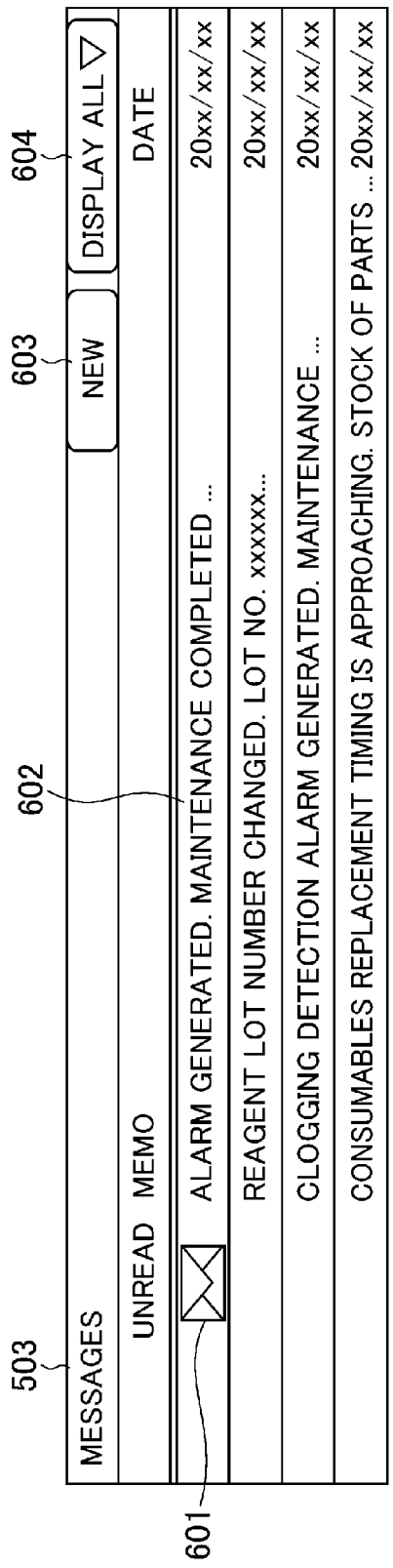
FIG. 3 is an explanatory diagram of another operation screen displayed on the display/input section in the automatic analyzer according to the embodiment of the present invention.

First, details of the maximized workflow display in the automatic analyzer according to the embodiment of the present invention is described below with reference to FIGS. 2 and 3.

The maximized workflow display screen shown in FIG. 2 represents a system status screen, and the display screen mainly includes an operation guidance section 502 and a message list section 503.

Included besides the two main sections are a status display section 501 which represents a status of the apparatus, a date, and other information, a global menu display section 506 which indicates, for example, a measurement starting or ending instruction to the automatic analyzer, and a status-monitoring button display section 504 which includes various buttons such as Reagent, Samples Rack, Calibration, Data Monitor, and Quality Control.

Next, details of the operation guidance section 502 are described below. The message list section 503 will be described later herein referring to FIG. 3.

The operation guidance section 502 can be reread to mean a workflow display section. On the operation guidance section 502 of the system status display, a Set Up Reagent button, a Delete Sample button, a Calibration button, a Routine QC button, a Wait Reagent QC button, a Print Results button, a Save Results button, and a Maintenance button are arranged in the sequence of their process. In the operation guidance section 502, when the work flow representing the series of operations and works is displayed, these operations and works are displayed in the sequence that they are processed, and this display is referred to as the maximized workflow display.

In addition to the buttons for these operations and works of the work flow, buttons for other working steps can be arranged, in which case the other working steps refer to, for example, parameter downloading, recommended calibration, startup calibration, time-out QC, calibration/QC/loading-list printing, calibration result saving, and QC result accumulation.

While eight buttons are displayed in the example of FIG. 2, the number of working steps to be displayed on the screen can be changed automatically according to a skill level of an operator of the apparatus. The operator can use input means or the like to enter the skill level by himself or herself.

These buttons change a display color according to progress status of maintenance, a residual amount of reagent in the container, or other information. Based on these color information the operator continues the necessary work for the measurement. The operator can edit the working step buttons displayed in the operation guidance section 502. Edit operation on the buttons will be described later herein referring to FIG. 6.

The workflow display screen can be closed by operating a Close button 505 thereon when displaying the system status screen. In addition, operating a Reduce button 508 on the display screen shown in FIG. 2 switches the screen to the reduced workflow display shown in FIG. 4. When the control unit 312 in FIG. 1 detects that the Reduce button 508 has been operated, the display/input section 314 correspondingly presents the reduced workflow display.

The message list section 503 that enables necessary matters or items to be communicated between users is displayed in combination with the workflow operation display. Thus, the user at work efficiently can confirm a currently necessary work in a single operation.

When the apparatus starts, the system status screen shown in FIG. 1 is desirably displayed automatically so that the user can first obtain brief information on the apparatus status.

Next, the message list section 503 in the display of the system status screen is described in detail below referring to FIG. 3.

The message list section 503 displays a plurality of messages 602 in a list format. The messages 602 are displayed to confirm contents of the message to be sent to other operators. Moving a cursor to a message 602 will display all text of the message. A selected message can also be deleted. A mail icon 601 is displayed at an unread message. In addition, an appropriate icon can be displayed according to particular importance or urgency of the message.

A click of a Create a Message button 603 enables a message to be created and sent as well. Selectable choice includes an operator and service as a transmission destination.

A Refine Messages button 604 is used to narrow down messages 602 in the message list section 503 according to a type or status of messages. For example, if Display All is selected with the Refine Messages button 604, the messages 602 in the message list section 503 are all displayed. The refinement can likewise be done by selecting other buttons including Unread Messages Only, This Week only, Service, and Important.

Next, details of the reduced workflow display in the automatic analyzer according to the embodiment of the present invention is described below with reference to FIGS. 4 and 5.

Figure 4:
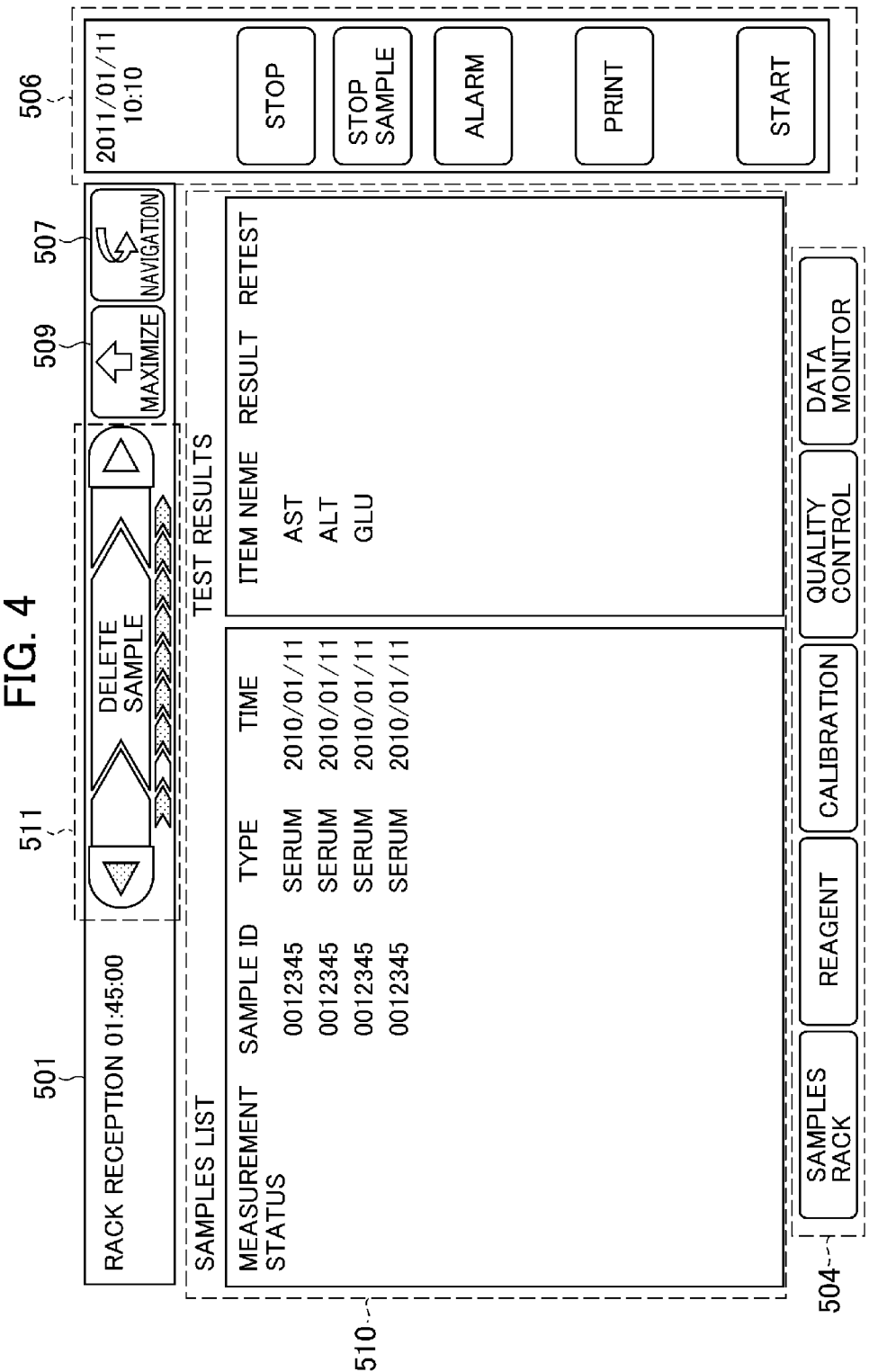
FIG. 4 is an explanatory diagram of yet another operation screen displayed on the display/input section in the automatic analyzer according to the embodiment of the present invention.
Figure 5:
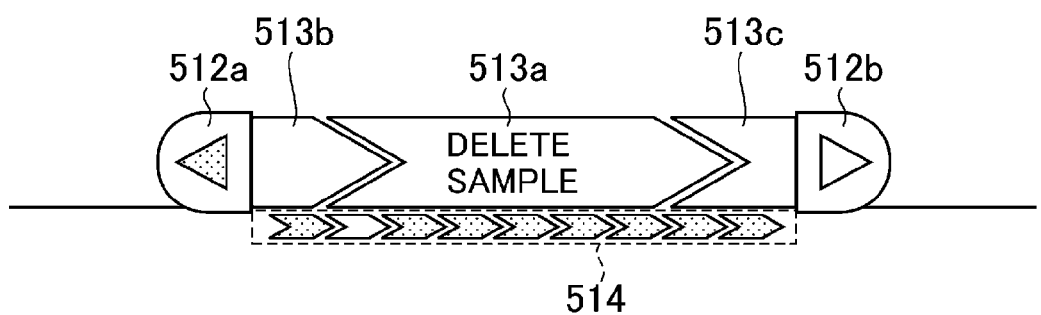
FIG. 5 is an explanatory diagram of a further operation screen displayed on the display/input section in the automatic analyzer according to the embodiment of the present invention.

The reduced workflow display screen shown in FIG. 4 represents a samples list screen, and the display screen mainly includes a setting/input display section 510. Included in addition to this section are a status display section 501 which represents status of the apparatus, a date, and other information, a global menu display section 506 which indicates, for example, a measurement starting or ending instruction to the automatic analyzer, and a status-monitoring button display section 504 which includes various buttons such as Reagent, Samples Rack, Calibration, Data Monitor, and Quality Control.

In the present example, a reduced workflow display section 511, or a reduced display of work flow, is presented as a part of the status display section 501. When the apparatus is measuring data, the status display section 511 shows such information as an estimated analytical completion time relating to selected sample information and always presents the reduced workflow display automatically under a standby state.

Selection of a Maximize button 509 in FIG. 4 shifts the screen to the maximized workflow display screen shown in FIG. 2.

Next, details of the reduced workflow display section 511 are described below referring to FIG. 5.

Working Step buttons 513 (513a, 513b, 513c) display the working steps constituting the work flow. It is difficult to display all work information concerning the work flow inside the display; however, at least one working step is displayed. Selection of the Working Step button 513b on the reduced workflow display section 511 displays Delete Sample as a specific operation or work. Additionally, if the working steps exist that immediately precede and immediately follow the selected operation (work), these working steps are displayed in symbol form as the Working Step buttons (513a, 513c). That is to say, in this example the three working steps are shown, and text is displayed only for the working step 513a located in the middle of the three. The number of working steps to be displayed may be fixed beforehand, or the number of working step to be displayed can be set by a user through the screen optionally.

A click of any of the working step buttons 513 (513a, 513b, 513c) on the screen moves screen control to a corresponding work screen. In the example of FIG. 4, after the click of the Delete Sample button, a Samples List and Test Results are displayed in the setting/input display section 510, so that a desired sample can be deleted by selecting it from the Samples List.

When a work to be done is displayed at the working step button 513a, the working step and display color corresponding to the working step button 513a are automatically discriminated according to a particular level of necessity or urgency as in the case of a workflow operation on the system status display.

A click of the previous or next working step button without text, as in a case of the working step button 513b or 513c, will automatically move the button to the middle and display full text of the working step. For example, when as shown in the operation guidance section 502 of FIG. 2, the working step before Delete Sample is the Set Up Reagent step, and the working step after Delete Sample is the Calibration step, a click of the working step button 513b displays text of the Set Up Reagent step at the position of the working step button 513a. A click of the working step button 513c will instead display text of the Calibration step at the position of the working step button 513a.

An overall-flow indicator 514 indicates where in the entire work flow the working step 513a displayed in the middle is placed.

In this manner, the reduced workflow display section 511 uses the working step buttons 513 (513a, 513b, 513c) and the overall-flow indicator 514 to show details of a specific operation or work and where in the overall processing sequence the specific operation or work is placed.

Scroll buttons 512 (512a, 512b) are input means provided to move the screen from the displayed working step to the previous or next working step.

If (other) working steps to be processed in the work flow is in the previous or next working step, a direction in which the work flow is to be shifted may be automatically identified by a color according to the level of necessity or urgency. Thus, the system reliably guides the user to the desired working step. For example, if the working step corresponding to the scroll button 512b has a higher level of necessity than that of the working step corresponding to the scroll button 512a, the scroll button 512b is displayed in red to indicate that the user can readily understand that the particular working step is higher in the level of necessity.

On the contrary, if the display color of the scroll button 512 remains unchanged, since the user can recognize that no other necessary working step exists he or she can cut the need of going through all the work steps.

Therefore, if for example the scroll button 512a is displayed in red to indicate urgency, and the scroll button 512b is displayed in gray to indicate a standard state, the user can move to the necessary working step by pressing the scroll button 512a.

A click of the Maximize button 509 will switch the reduced display of the work flow in the reduced workflow display section 511 to the maximized display shown in FIG. 2. The Maximize button 509 may be reread to mean an expand button, in which case an expanded work flow can be displayed uppermost.

A Workflow Call/Close button 507 changes or closes the workflow display depending on a display status of the workflow. For example, the system status screen can be closed by clicking the Workflow Call/Close button 507 when the system status screen is open.

In addition, when there is information such as a warning, calling attention, and announcement, the user could easily be aware of the information through an displayed icon and a button with its color changed before opening the screen. For example, if a message to be sent to other operators exists in an unread state, this can be notified to the user by change of the icon display of the Workflow Call/Close button 507 to a display of an email icon, for example.

Besides the display relating to workflow operations, the system status screen enables irregular job information or special notes, such as maintenance service information and message contents exchanged between users, to be communicated as messages between these users on the operation screen.

Next, details of a workflow edit screen displayed on the display/input section in the automatic analyzer according to the embodiment of the present invention are described below referring to FIG. 6.

Figure 6:
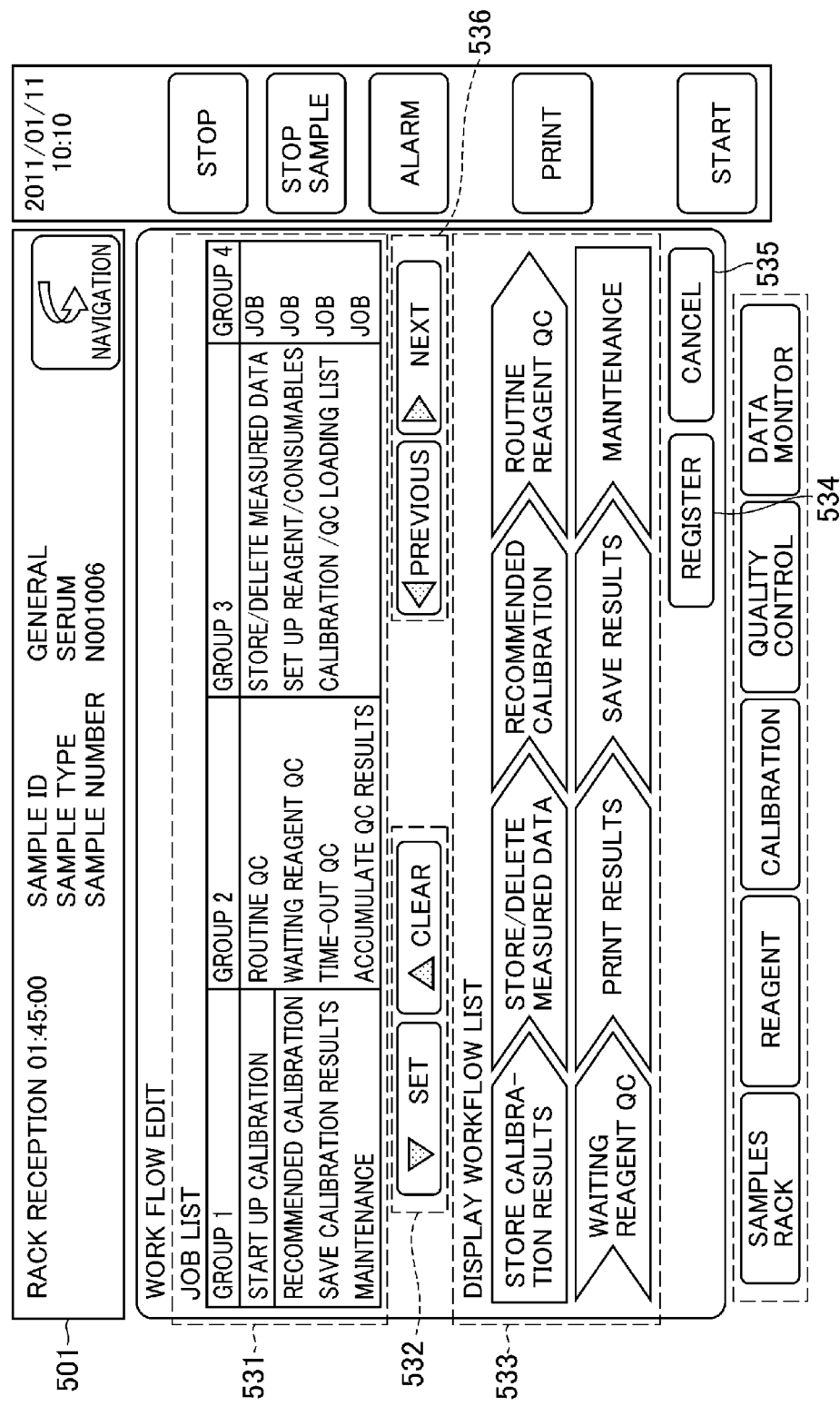
FIG. 6 is an explanatory diagram of a workflow edit screen displayed on the display/input section in the automatic analyzer according to the embodiment of the present invention.

FIG. 6 is an explanatory diagram of the workflow edit screen displayed on the display/input section in the automatic analyzer according to the embodiment of the present invention.

The number of elements constituting the work flow to be displayed, working step description or contents, the processing sequence, and other information on the work flow can be edited according to usage conditions of a facility in which the automatic analyzer is installed. The maximum number of elements which can be registered, however, depends also on the screen composition and other factors. The workflow edit screen includes a job list select section 531, a job list select button section 532, a workflow list display section 533, and a re-sequence button 536 that edits the processing sequence of the working steps in the work flow.

When a working step is selected in the job list select section 531 and a Set button is selected in the job list select button section 532, the corresponding display is reflected in the workflow list display section 533.

After this, when a working step is selected in the workflow list display section 533, and a Release button is selected in the job list select button section 532, the working step that has been selected in the workflow list display section 533 is released.

The edited work flow can be registered using a Register button 534 or canceled using a Cancel button 535.

The workflow edit screen shown in FIG. 6 can be started from a System Setup Screen. Whether the work flow needs editing is considered to usually depend on the facility in which the automatic analyzer is installed. It is assumed, however, that the work flow, once set, will seldom be changed. The workflow edit screen can therefore be started by operating the buttons provided under the Workflow Edit on the system setup screen. The system setup screen refers to a screen relating to apparatus operation, management, and maintenance. More specifically, this screen relates to, for example, registering batch preparatory steps for combining necessary maintenance items and executing each at the same time, and setting a method of sample ID management.

As described above, the present embodiment enables the maximized workflow display and the reduced workflow display to be selectively displayed and thus the user to save the time and labor associated with a screen shift and efficiently advance the processing of the working steps without alternating display screens as well as omitting any complex works and turning back screens necessary for the measurement.

In addition, since the maximized workflow display and the reduced workflow display can be easily switched therebetween, providing easily understandable work flow and reliability of measurement results can be ensured regardless of the skill level of the user as an operator of the apparatus.

Further, precaution or message contents exchanged between users or sent from a service can be confirmed on the same screen as that of the maximized workflow display. This enables the user to simultaneously confirm such precaution and message contents along with a necessary work, thereby improving operational convenience.

Furthermore, even in the reduced workflow display, the user can scroll (move) from the displayed working step to other working step, which in turn enables the user to perform the same operations as in the maximized display of the work flow.

Moreover, since the reduced workflow display is constantly presented in whatever job screen opened by the user, the work flow and the desired operation screen can be viewed on the same screen without a screen shift. This enables the user to reliably advance the processing of the working steps without alternating display screens as well as omitting any complex works and turning back screens necessary for the measurement, and hence to obtain reliable measurement results.

Besides, since the reduced workflow display merely presents the reduced display form in a part of the status-only display area displayed in conventional technology, both the screen composition and software can be changed without considerable amount of time and labor.

DESCRIPTION OF REFERENCE CHARACTERS

102 . . . Transport unit
107 . . . Rack
108 . . . Sample container
310 . . . Reagent container
301 . . . Reagent disk
309 . . . Constant-temperature oven
304 . . . Reaction vessel
303 . . . Reagent-dispensing pipettor
308 . . . Sample suction position
302 . . . Reagent-dispensing pipettor
305 . . . Reaction disk
306 . . . Multi-wavelength photometer
307 . . . Analog/digital converter
311 . . . Stirrer
312 . . . Computer
314 . . . Display/input section
501 . . . Status display section
502 . . . Operation guidance section
503 . . . Message list section
504 . . . Status-monitoring display section
505 . . . Workflow Screen Close button
506 . . . Global menu display section
507 . . . Workflow Call/Close button
508 . . . Reduce button
509 . . . Maximize button
510 . . . Setting/input display section
511 . . . Reduced workflow display section
512a, 512b . . . Scroll buttons
513a, 513b, 513c . . . Working step buttons
531 . . . Job list select section
532 . . . Job list select button section
533 . . . Workflow list display section
534 . . . Register button
535 . . . Cancel button
536 . . . Re-sequence button
514 . . . Overall-flow indicator
601 . . . Email icon
602 . . . Message
603 . . . Create a Message button
604 . . . Refine Messages button

The invention claimed is:

1. An automatic analyzer, comprising:
a photometer configured to analyze a reaction solution within a reaction vessel; and
a computer connected to a display unit and the photometer, wherein the computer is programmed to selectively display a maximized workflow display on the display unit and a reduced workflow display on the display unit that represents a series of operations,
wherein the computer is programmed to display the maximized workflow display to show the series of the operations in an order that the operations are processed of an overall processing sequence,
wherein the computer is programmed to display the reduced workflow display on the display unit, the reduced workflow display comprising:
a setting/input display section,
a working step button, representing a corresponding operation, the working step button displaying text of an operation of the operations represented in the maximized workflow, wherein the computer is programmed to display a work screen on the setting/input display section when the working step button is selected
a scroll button, wherein the computer is programmed to display another working step button displaying text of another operation corresponding to the operation that an adjacent working step button represents when the scroll button is selected, and
an overall-flow indicator display that displays an indication of a position of an operation in the overall processing sequence.

2. The automatic analyzer according to claim 1,
wherein the computer is programmed to display, on the display unit in the reduced workflow display, the working step button using text in a center position and adjacent working step buttons without using text in adjacent positions of the center position, wherein the working step button is displayed in the center position between the adjacent working step buttons in the adjacent positions, and
wherein the computer is programmed to display, on the display unit in the reduced workflow display, when the adjacent working step button is selected, the selected adjacent working step button in the center position of the working step button with text related to the selected adjacent working step button.

3. The automatic analyzer according to claim 1, wherein the computer is programmed to display, on the display unit created/stored messages along with the maximized workflow display.

4. The automatic analyzer according to claim 3, wherein the computer is programmed to store messages that are selectively displayed according to a type or status of the messages.

5. The automatic analyzer according to claim 3, wherein the computer is programmed to display messages including an unread message, the unread message being displayed with a symbol in distinction from other messages.

6. The automatic analyzer according to claim 1, wherein the computer is programmed to edit the processing order of the operations or contents of the operations displayed on the maximized workflow display.

7. The automatic analyzer according to claim 1, wherein the computer is programmed to display information on other screens of the display unit simultaneously with the reduced workflow display.

8. The automatic analyzer according to claim 1, wherein the computer is programmed to display a color of the working step button of the reduced workflow display according to a level of necessity or urgency.

* * * * *